US008778612B2

(12) United States Patent
Kempin et al.

(10) Patent No.: US 8,778,612 B2
(45) Date of Patent: Jul. 15, 2014

(54) METHOD FOR QUANTITATIVELY DETERMINING A NUMBER OF ANALYTES

(75) Inventors: Uwe Kempin, Leipzig (DE); Thomas A. Keller, Leipzig (DE)

(73) Assignee: PE Diagnostik GmbH (DE)

( * ) Notice: Subject to any disclaimer, the term of this patent is extended or adjusted under 35 U.S.C. 154(b) by 2734 days.

(21) Appl. No.: 10/508,113

(22) PCT Filed: Mar. 7, 2003

(86) PCT No.: PCT/DE03/00745
§ 371 (c)(1), (2), (4) Date: May 19, 2005

(87) PCT Pub. No.: WO03/079011
PCT Pub. Date: Sep. 25, 2003

(65) Prior Publication Data

US 2006/0246435 A1 Nov. 2, 2006

(30) Foreign Application Priority Data

Mar. 16, 2002 (DE) ................................ 102 11 818

(51) Int. Cl.
*G01N 33/53* (2006.01)

(52) U.S. Cl.
USPC ............................................ 435/7.1; 435/7.2

(58) Field of Classification Search
None
See application file for complete search history.

(56) References Cited

U.S. PATENT DOCUMENTS 4,098,876 A * 7/1978 Piasio et al. .................. 436/500
4,197,361 A * 4/1980 Hoff et al. ......................... 435/5
4,587,223 A * 5/1986 Soini et al. .................... 436/536
5,753,430 A * 5/1998 Mehta et al. ...................... 435/5
5,958,202 A * 9/1999 Regnier et al. ................ 204/451
6,083,763 A 7/2000 Balch
6,093,796 A * 7/2000 Tindall et al. ................. 530/324
6,352,694 B1 * 3/2002 June et al. .................. 424/93.71
6,670,196 B1 * 12/2003 Buechler ....................... 436/518
2003/0073141 A1 * 4/2003 Hubner-Parajsz et al. .. 435/7.21

OTHER PUBLICATIONS

Plowman et al., "Multiple-analyte fluoroimmunoassay using an integrated optical waveguide sensor", Anal. Chem., 1999, vol. 71, pp. 4344-4352.*
Wiese et al., "Simultaneous Multianalyte ELISA performed on a microarray platform", Clin. Chem., 2001, vol. 47, pp. 1451-1457.*
Wiese et al., Clinical Chemistry 47/8. Aug. 2001, pp. 1451-1457.

* cited by examiner

*Primary Examiner* — Jacob Cheu
(74) *Attorney, Agent, or Firm* — Roger D. Emerson; Emerson Thomson Bennett, LLC

(57) ABSTRACT

A method for the quantitative assay of n different analytes, where n is at least 2, is provided. The method consists of the following steps: (a) At least one labeled detector-binding partner is added to a test sample containing the analytes. This leads to the formation of detector-analyte complexes, each of which consists of one analyte molecule and one detector molecule. The number of detector binding partners x equals n−1. Each detector-binding partner binds to at least one analyte. At least one of the detector-binding partners can bind to at least two analytes. (b) The detector-analyte complexes formed in step (a) bind to capture-binding partners and form detector-analyte-capture complexes. The number of capture-binding partners y equals the number n of the analytes. Each capture-binding partner is specific for at least one detector-analyte complex. (c) The time-resolved formation of the detector-analyte-capture complexes is measured.

3 Claims, 10 Drawing Sheets

6 7 8 5
surface region surface region surface region 9
12 11 10
13 14 15
surface region surface region surface region 9
12 11 10

Time—resolved increase of the fluorescence signal as the result of the binding of detector-fPSA-complexes to two different surface regions.

Time—resolved increase of the fluorescence signal as the result of the binding of detector-PSA—ACT complex to the surface region.

Time—resolved increase of the fluorescence signal as the result of detector-fPSA complex binding and detector-PSA-ACT complex binding to two different surface regions.

METHOD FOR QUANTITATIVELY DETERMINING A NUMBER OF ANALYTES

This US utility application is a national phase application which claims priority from PCT/DE03/00745, filed Mar. 7, 2003, which claims priority from German Patent DE 102 11 818.3, filed Mar. 16, 2002, respectively.

I. BACKGROUND OF THE INVENTION

A. Field of Invention

The invention pertains to a method for the quantitative assay of multiple analytes. In particular, the invention pertains to the quantitative affinity assay of multiple analytes based on the specific binding of analytes to their binding partners.

B. Description of the Related Art

For some time now, affinity assays have been used to determine the quantity of chemical and biochemical compounds (analytes). Such tests may include the use of fluorescence immunoassays as well as fluorescence immunosensors.

Document DE 196 28 002 has established methods for the simultaneous assay of multiple analytes. Analyte specific antibodies are used for a sandwich assay. According to specificity, the antibodies are immobilized separately and consecutively in different regions within a range of exposure.

The sample with the analytes and differently labeled, analyte specific antibodies are placed in a container. The number of the antibodies must equal the number of analytes in the assay. The different analyte specific labeled antibodies bind to different locations within the exposure range, dependent on the localization of the earlier immobilized analyte specific antibodies. The quantity of the analytes is determined by time- and space-resolved fluorimetry.

It follows that in this procedure each analyte requires exactly one analyte specific antibody and one immobilized antibody, which itself also has to be analyte specific. As a rule, the use of different labeled antibodies necessitates different excitation wavelengths or space-resolved measurements. Accordingly, the setup for the measurement has to be complex.

In this context, the different labeled antibodies are either different antibodies labeled with different dyes or, alternatively, different antibodies labeled with identical dyes.

II. SUMMARY OF THE INVENTION

It is the objective of this invention to use current state of technology for the removal of the disadvantages noted above. Specifically, a more efficient method for the quantitative assay of multiple analytes shall be defined.

Under the provisions of this invention, a method for the quantitative assay of at least two or more different analytes is proposed. The method involves the following steps:

(a) At least one labeled detector-binding partner is added to a sample, which contains n analytes. This leads to the formation of detector-analyte complexes, which each consist of one analyte and at least one detector molecule. The number of detector-binding partners x equals n−1. Each of the detector-binding partners can bind to at least one analyte, and at least one of the detector-binding partners can bind to at least two analytes.

(b) The detector-analyte complexes obtained in step (a) bind to capture-binding partners and form detector-analyte-capture complexes. The number of capture-binding partners y is equal to the number of analytes n, and each capture-binding partner is specific for at least one detector-analyte-complex.

(c) The time-resolved formation of the detector-analyte-capture complexes is measured.

In contrast to current procedures, the proposed method requires fewer than n detector-binding partners in a simultaneous quantitative assay, which contains n analytes. Preferentially, only one detector-binding partner is used. This applies even if the number of analytes is larger than 2.

In comparison with current procedures, the time-resolved detection of the detector-analyte-capture complex formation in step (c) can be adapted to fewer detector-binding partners. The quantitative assay of the analytes is much simpler because fewer detector-binding partners are used. When only a single detector-binding partner is used the quantitative assay becomes especially simple. This allows the use of a simplified technical setup for the quantitative assays.

In step (a), the detector-binding partners may be incubated with the analytes either simultaneously or consecutively to form detector-analyte complexes. The detector-analyte complexes formed in step (a) may consist of one analyte molecule and at least one detector molecule, i.e. certain analytes, (e.g. proteins, such as creatine kinase BB (CK-BB), immunoglobulin E (IgE) or C-reactive protein (CRP)) can bind several identical detector-binding partners.

In step (a), at least a third binding partner can be added to the assay. This third partner must be specific for an analyte, and it must bind to a site on the analyte, which is different from the binding sites for the detector-binding partners. In this form of the assay, the detector-analyte complexes include the third binding partner. In step (b) the detector-analyte complexes bind via the third binding partner to the immobilized capture-binding partner, which is specific for the analyte.

In one of the applications, at least one of the detector-analyte-complexes binds to at least two different capture-binding partners. It is also possible that two different detector-analyte complexes bind to one capture-binding partner. This makes it possible to assess the quantities of a group of detector-analyte complexes.

The detector-binding partners are preferably labeled with fluorescent or luminescent dyes.

Detector-binding partners, capture-binding partners and third binding partners, which are suitable for the methodology described in this invention may be ligands, polyclonal and monoclonal antibodies and their antigen-binding fragments, RNA, DNA, DNA and RNA derivatives and their analogues, such as aptamers, allergens or proteins, such as lectins.

Preferably, the capture-binding partners are immobilized on different regions of a surface. The capture-binding partner may bind to a surface either directly via hydrophobic interactions, ionic interactions or via chemical bonds. However, a facilitator molecule on the surface, such as an anti-antibody, avidin or a carrier protein can also mediate the immobilization via indirect bonds. Capture-binding partners may also be immobilized via binding to a spacer.

Detector-analyte complexes are brought in contact with different immobilized capture-binding partners at different surface regions. Detector-analyte-capture complexes are then formed through binding of detector-analyte complexes to the different capture-binding partners at different surface regions.

The formation of detector-analyte-capture complexes is determined as a function of time. This can be done, for example, by performing at least two measurements at different time intervals or through measurements at the end point of the detector-analyte-capture complex formation.

In both cases, the increase in the measured indicator value is used for the quantification. In case of fluorescence labeled detector-binding partners, fluorescence signals serve as the measured indicators. It is sufficient to measure the increase of the indicator value to determine the quantity of the analyte.

As described in Anal. Chem. 1999, 5430-5435, in WO 98/41843 (DE 197 11281) and also in WO 98/02732, an optical sensor system may be used for the assay. For this method the detector-binding partners are labeled with a fluorescent dye. The sample containing the analytes is incubated with the detector-binding partners of choice. This leads to the formation of different detector-analyte complexes (analyte1-detector1, analyte2-detector1, analyte3-detector2, analyte4-detector2, anlyte5-detector2, . . . ) The solution is then allowed to flow over the different surface regions with the immobilized capture-binding partners. The detector-analyte complexes bind to the immobilized capture-binding partners.

The detector-analyte complexes that are bound to the capture sites are labeled with a fluorescent dye. The excitation of this dye is achieved using an evanescent field, which is created using a laser. This evanescent field is created as a result of total internal reflection of the laser beam at the boundary of the highly refractive surface material (e.g. PMMA) and the low refractive sample material.

The intensity of the evanescent field diminishes exponentially with the distance from the surface. As a result, only those fluorescence labeled complexes emit fluorescent light, which have formed a sandwich with their respective capture-binding partners on the surface. Labeled complexes outside the evanescent field are not excited and do not contribute to the fluorescent light.

The number of sandwich complexes (i.e. detector-analyte-capture complexes) formed per unit of time is directly proportional to the concentration of fluorescence labeled immune complexes. Therefore, the time-dependent increase in fluorescence signal is a measure of the analyte concentration in the sample. The increase of the fluorescence signals is measured for the different surface regions and used to determine the initial increase in mV/s.

Calibration is done with a known quantity of the analyte to be studied. Results from the measurements of different analytes in a test sample are then correlated with the data from the calibration curve. Thus, a qualitative and quantitative result is obtained for the presence of analytes in a test sample.

The method according to this invention can be used to assay different groups of analytes. Given below are examples for such groups of analytes. As a basic precondition, the analytes must contain either an identical subunit or a cross-reacting region.

The proposed method can be applied to simultaneously assay the creatine kinase MB (CK-MB) and creatine kinase BB (CK-BB). In this assay, a specific detector-binding partner is chosen, which recognizes CK-MB as well as CK-BB. The first capture-binding partner in this assay is specific for CK-MB but does not recognize CK-BB, while the second capture-binding partner is specific for CK-BB but does not recognize CK-MB.

That makes the number of analytes 2, the number of detector-analytes is 1, and the number of capture-binding partners is 2. In this assay, the CK-MB concentration is measured at the first surface region, and the CK-BB concentration is determined at the second surface region.

Alternatively, creatine kinase MB (CK-MB) and creatine kinase BB (CK-BB) can also be assayed as follows:

As described above, the chosen detector-binding partner recognizes CK-MB as well as CK-BB and the first capture binding-partner is specific for CK-MB while it does not recognize CK-BB. However, the second capture-binding partner recognizes both, CK-MB as well as CK-BB. This capture-binding partner is specific for the B subunit in CK-MB and CK-BB.

As before, this form of the assay contains 2 analytes, there is 1 detector-binding partner, and the number of capture-binding partners is 2. In this assay, the measurements for the first surface region yield the concentration of CK-MB and the measurements for the second surface region yield the sum of the CK-MB and CK-BB concentrations.

The proposed method can also be used for the simultaneous assay of at least two of the analytes, which are chosen among luteinizing hormone (LH), follicle stimulating hormone (FSH), thyroid stimulating hormone (TSH) and human chorionic gonadotropin (hCG). The selected detector-binding partner is specific for the alpha subunit, which is identical in all analytes of this group. The capture-binding partner is specific for the alpha subunits of the analytes.

The proposed method can further be used to simultaneously assay different isomeric forms of proteins. In the example, nicked hCG and non-nicked hCG are assayed. The chosen detector-binding partner recognizes both isomers, it specifically recognizes the alpha subunit. In this example, the first capture-binding partner recognizes only the non-nicked hCG, while the second capture-binding partner selectively recognizes nicked hCG.

This accounts for two analytes, there is one detector-binding partner, and the number of capture-binding partners is 2.

The proposed method can also be used for the simultaneously assay of immunoglobulin E antibodies (total IgE) and allergen specific IgE antibodies in a sample. Particularly in allergy diagnostics, this type of IgE assay is essential.

For the determination of total IgE and allergen specific IgE, the detector-binding partner consists of an IgE specific antibody. For example, the antibody IgE 60-4-4 (commercially available from pe-Diagnostik) can be used as detector-binding partner to assay human IgE. For the assay of total IgE, the above-mentioned antibody 60-4-4 or alternatively, IgE 27-1-4 (commercially available from pe-Diagnostik) is used as an immobilized, in a surface region localized capture-binding partner. A number of allergens are immobilized as capture-binding partners, each in a separate surface location. This creates localized binding sites for IgE, which specifically binds to any one of these immobilized allergens.

In the course of the assay, the detector-binding partners are first incubated for a few minutes with the test sample, which contains the analytes, i.e. the different allergen specific IgE antibodies. In this step the detector-binding partner binds to the analytes and detector-analyte complexes form with the different analytes.

This solution is then allowed to flow over the surface with its different binding regions. Each region exposes a different immobilized capture-binding partner. The binding of detector-analyte complexes to the capture-binding partners is measured as increase in fluorescence as a function of time.

The method according to this invention can also be used to simultaneously assay samples, which contain free prostate specific antigen (fPSA) and prostate specific antigen complexes with alpha anti-chymotrypsin (PSA-ACT). The sample may also contain the analyte human kallikrein-2 (hK2).

The quantitative assay for fPSA, PSA-ACT and human kallikrein-2 (hK2) then consists of the following steps:

(a) A sample with fPSA, PSA-ACT and hK2 is incubated with a labeled detector-binding partner and detector-analyte complexes are formed, which each consist of one analyte molecule and one detector molecule.

(b) The detector-analyte complexes formed in step (a) bind to three capture binding partners and form detector-analyte-capture complexes. In this assay, each capture-binding partner is specific for one detector-analyte complex.

(c) The time-resolved formation of the detector-analyte-capture complexes is measured.

An alternative method for the quantitative assay of fPSA, PSA-ACT and hK2 consists of the following steps:

(a) A labeled detector-binding partner is added to a sample with fPSA, PSA-ACT and hK2. As a result, detector-analyte complexes are formed, which contain one analyte molecule and one detector molecule each.

(b) The detector-analyte complexes formed in step (a) bind to three capture binding partners and form detector-analyte-capture complexes. In this assay, one capture-binding partner is specific for detector-fPSA complexes, another is specific for detector-hK2 complexes and the third binds detector-fPSA complexes as well as PSA-ACT complexes.

(c) The time-resolved formation of detector-analyte-capture complexes is measured.

The assay of only fPSA and PSA-ACT consists of the following steps:

(a) A labeled detector-binding partner is added to a sample with fPSA and PSA-ACT and detector-analyte complexes are formed, which each consist of one analyte molecule and one detector molecule.

(b) The detector-analyte complexes formed in step (a) bind to two capture binding partners and form detector-analyte-capture complexes. In this assay, one capture-binding partner is specific for detector-fPSA complexes, and the other binds detector-fPSA complexes as well as PSA-ACT complexes.

(c) The time-resolved formation of detector-analyte-capture complexes is measured.

The eventual presence of human kallikrein-2 in addition to fPSA and PSA-ACT in the sample does not interfere with this fPSA and PSA-ACT assay procedure.

III. BRIEF DESCRIPTION OF THE DRAWINGS

The invention may take physical form in certain parts and arrangement of parts; a preferred embodiment of which will be described in detail in this specification and illustrated in the accompanying drawings, which form a part hereof and wherein:

FIG. 1 shows step (a) of method 1 to assay fPSA, PSA-ACT and human kallikrein-2 (hK2).

FIG. 2*a* shows step (b) of method 1 to assay fPSA, PSA-ACT and hK2.

FIG. 2*b* shows a variation of step (b) of method 1 to assay fPSA, PSA-ACT and hK2.

IV. DESCRIPTION OF THE PREFERRED EMBODIMENT

Figure 1:
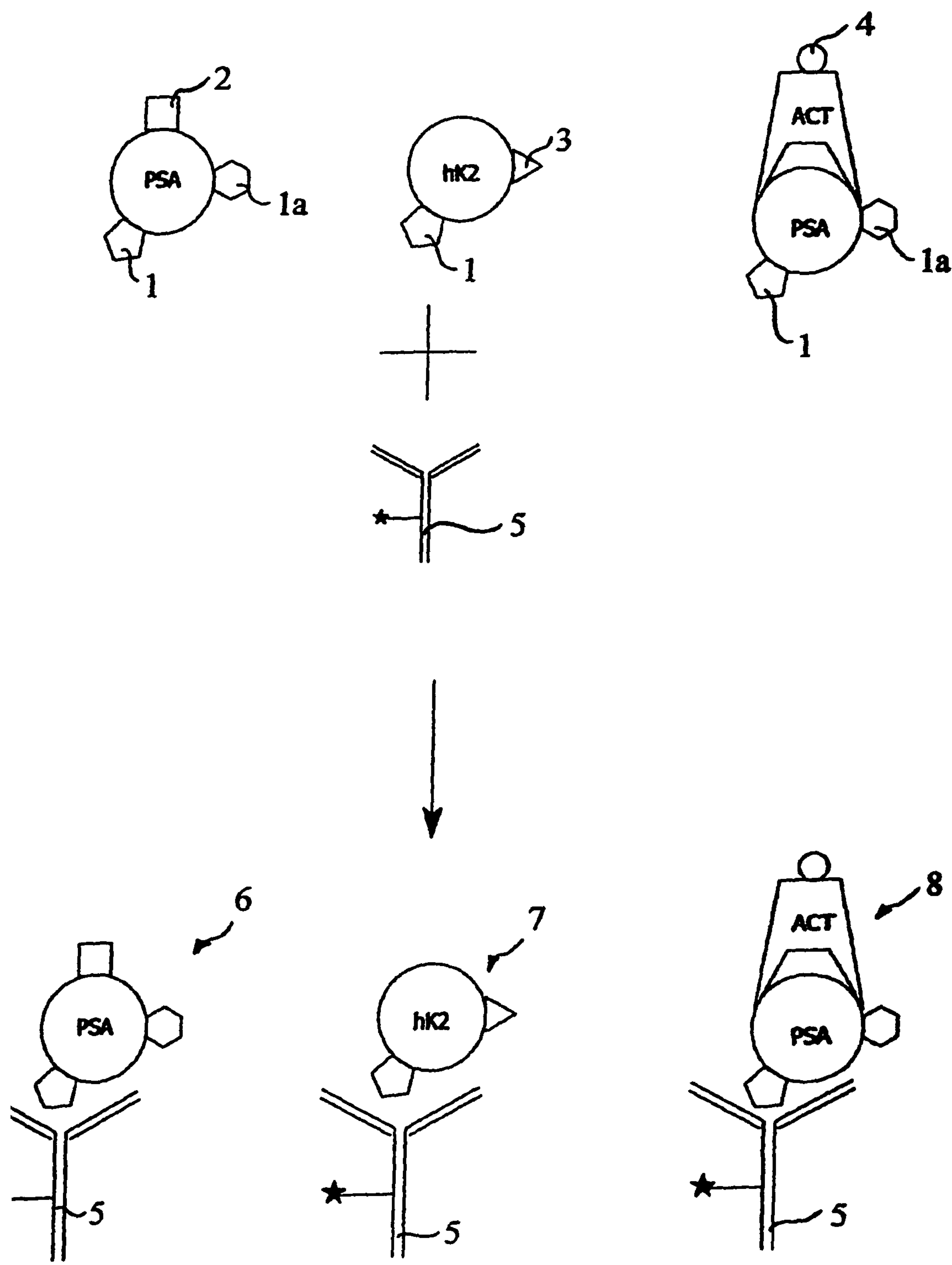

The following legend provides a list of reference characters and the items they represent for this description.

| Legend | |
|---|---|
| 1 | Binding site on either fPSA, hK2 or PSA-ACT |
| 1a | Binding site only on fPSA and PSA-ACT |
| 2 | Binding site only on fPSA |
| 3 | Binding site only on hK2 |
| 4 | Binding site only on ACT |
| 5 | Labeled detector-binding partner (label: *) |
| 6 | Detector-fPSA complex |
| 7 | Detector-hK2 complex |
| 8 | Detector-PSA-ACT complex |
| 9 | Surface |
| 10 | First surface region |
| 11 | Second surface region |
| 12 | Third surface region |
| 13, 13' | Detector-fPSA-capture complex |
| 14 | Detector-hK2-capture complex |
| 15, 15' | Detector-PSA-ACT-capture complex |
| 16 | Third binding partner |
| 17 | Detector-fPSA complex with the third binding partner |
| 18 | Detector-fPSA-capture complex with the third binding partner |

Figure 2A:
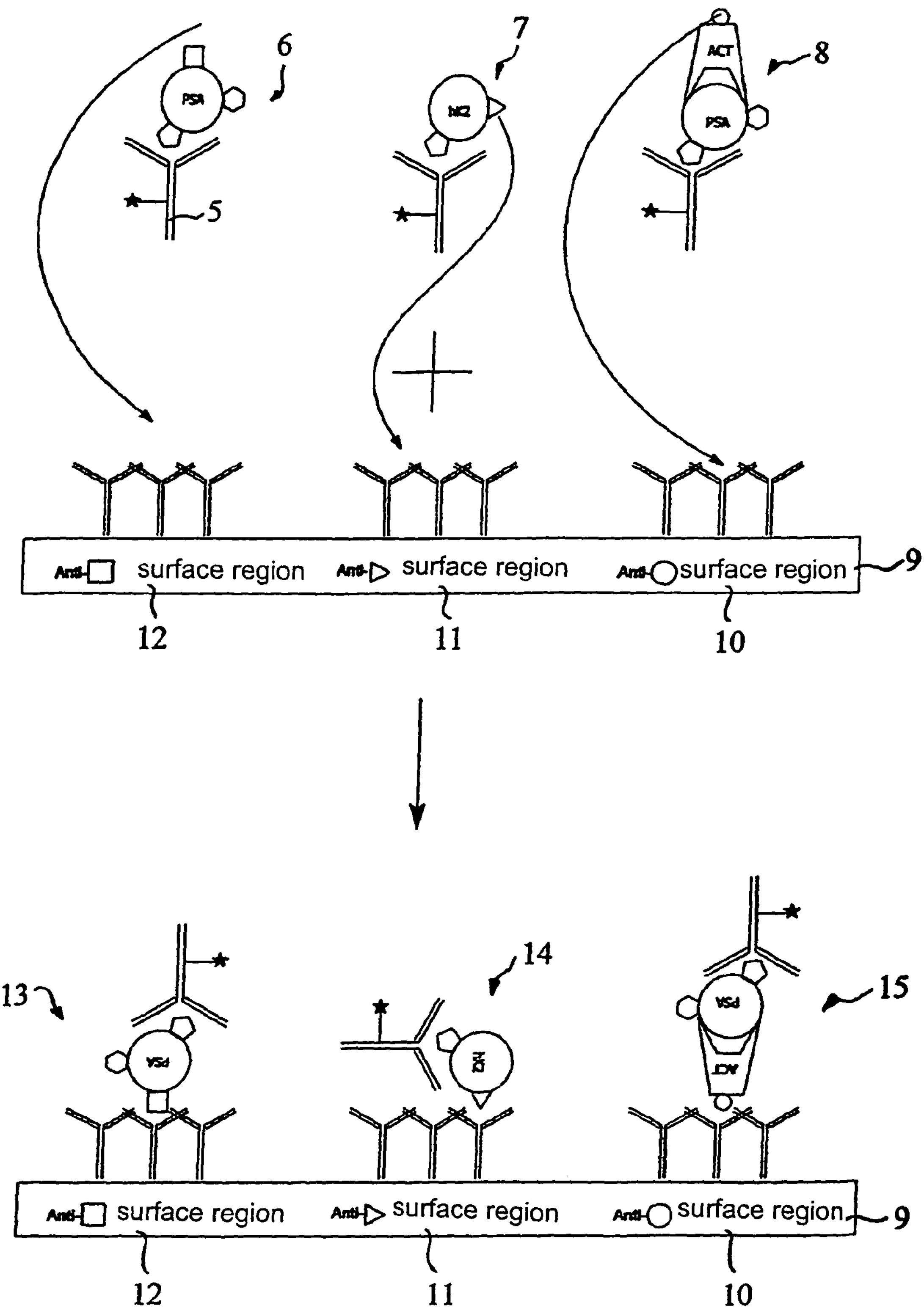
Figure 2B:
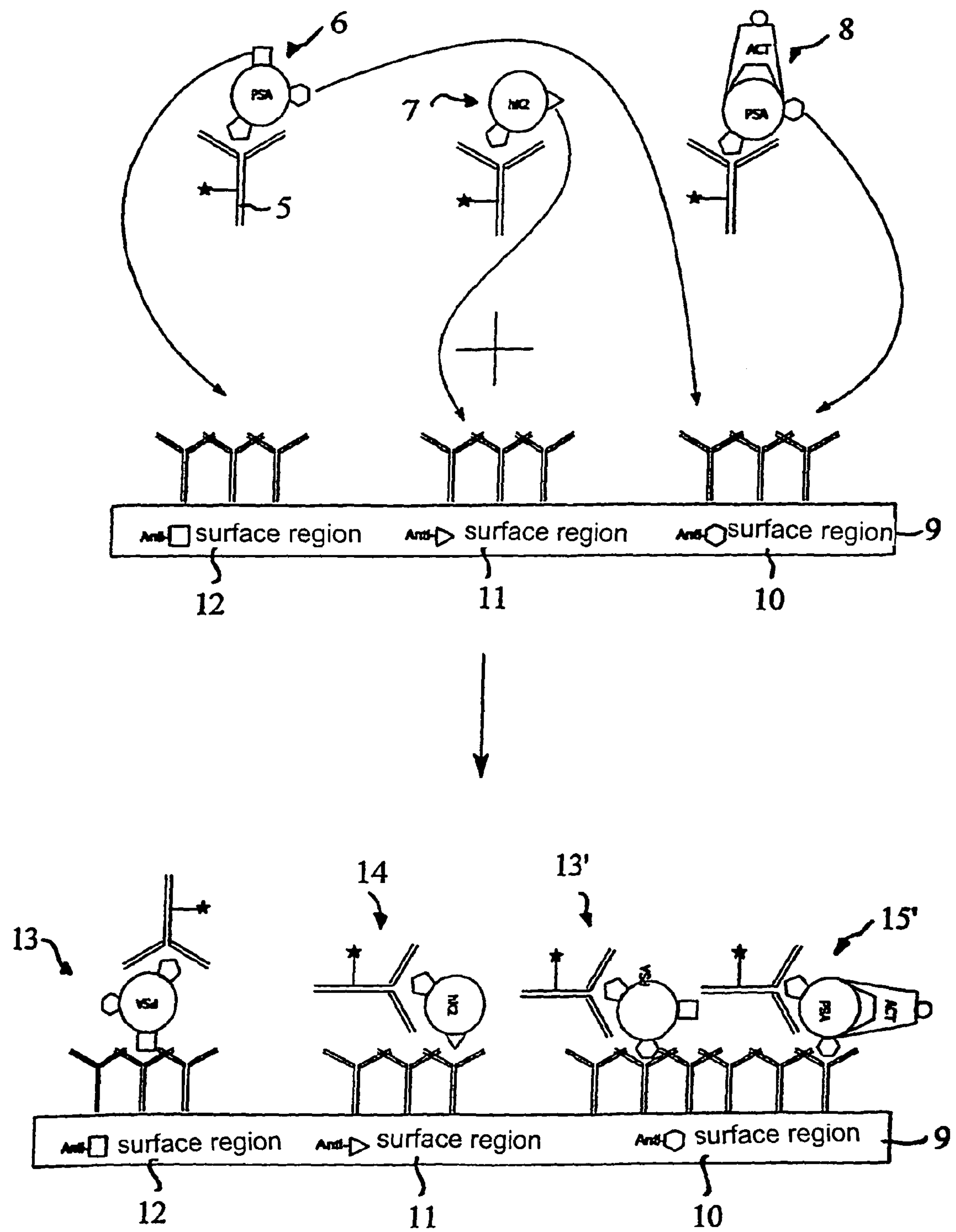
Figure 3:
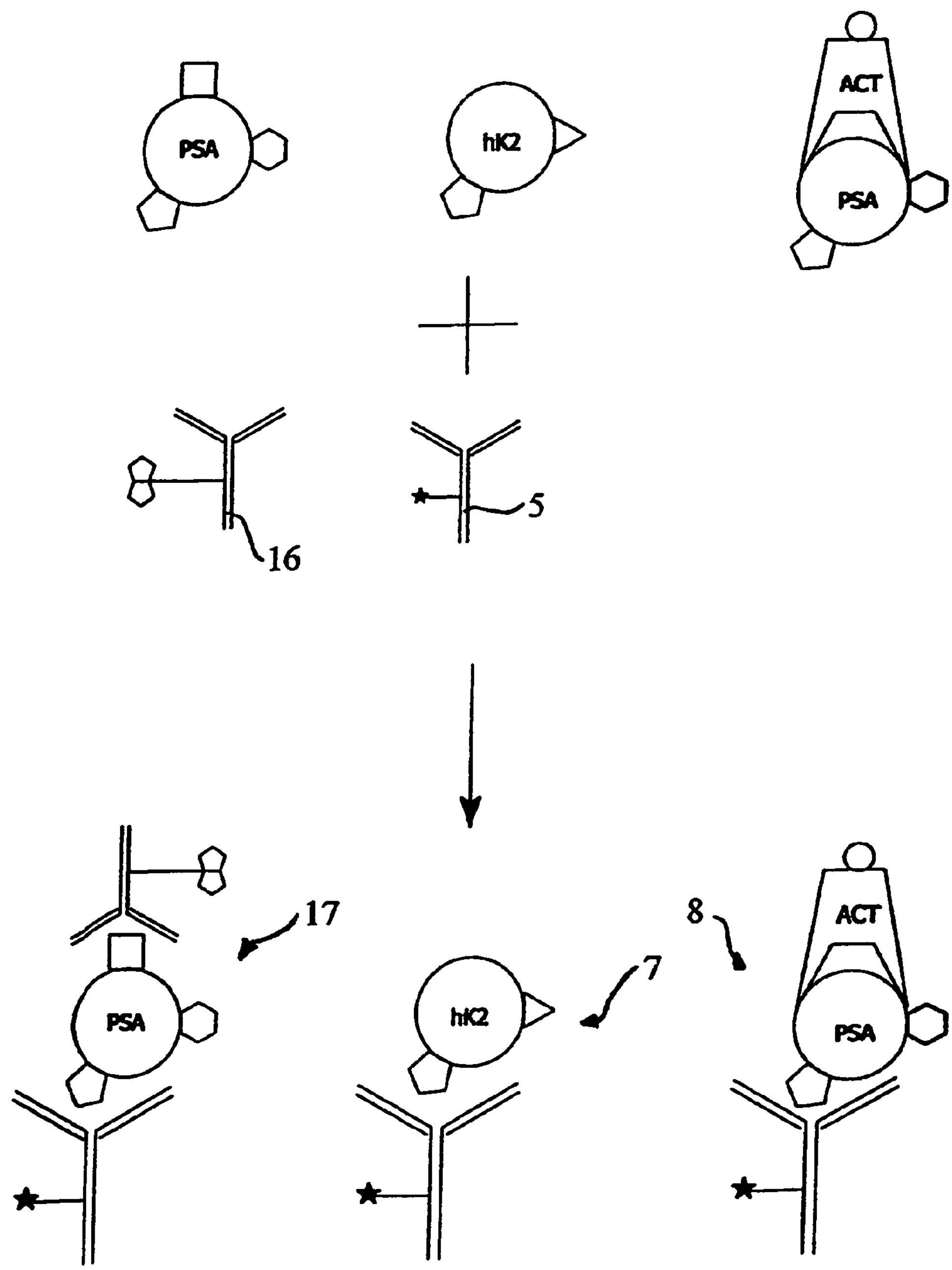
FIG. 3 shows step (a) of method 2 to assay fPSA, PSA-ACT and hK2.
Figure 4:
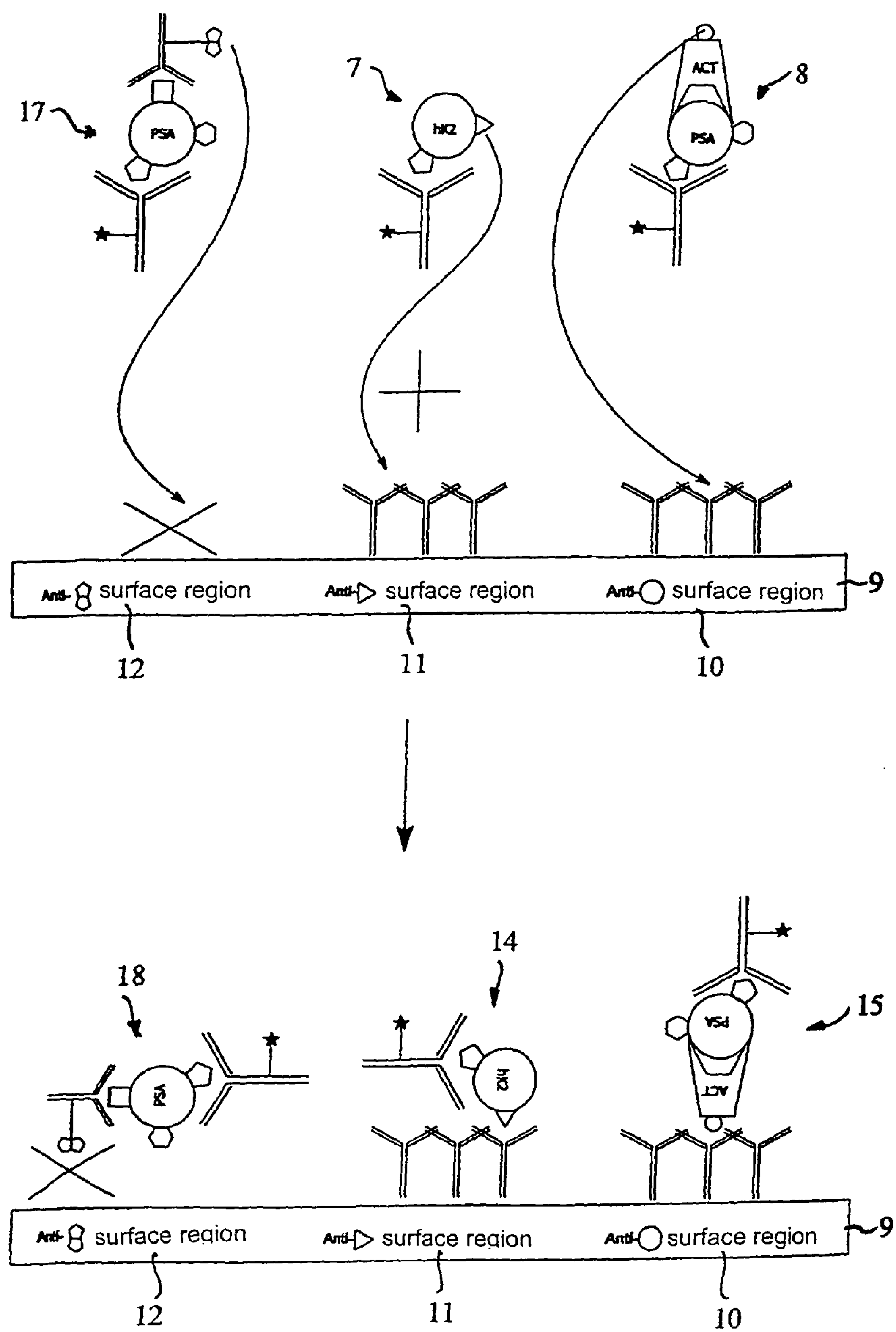
FIG. 4 shows step (b) of method 2 to assay fPSA, PSA-ACT and hK2.

FIGS. 1 through 4 show how the method according to this invention is applied to the quantitative assay of prostate specific antigens (PSA). This assay measures free PSA (fPSA), PSA in a complex with alpha-anti-chymotrypsin (PSA-ACT) as well as human kallikrein-2 (hK2) (FIGS. 1 and 3).

As seen in FIG. 1, a labeled binding partner 5 with the ability to recognize the binding site 1 (depicted as pentagon) is chosen as detector-binding partner. Binding site 1 is present on all analytes. The antibody PS 2 (HyTest) is suitable as detector-binding partner 5. PS 2 recognizes the PSA epitope 3 and strongly cross-reacts with human kallikrein-2. Other antibodies may be used as long as they have the same binding characteristics as described above for the detector-binding partner 5.

The antibody that is used as detector-binding partner 5 carries the label (*). Standard procedures are used to couple 0.001 to 10 (ideally 2-5) molecules of an activated fluorescent dye to this antibody. Examples of suitable fluorescent dyes for this purpose are (S 0458) (FEW Chemicals, Wolfen) or the cyan dye Cy5 (Amersham).

The sample with the analytes (fPSA, hK2 and PSA-ACT) is incubated for several minutes with the detector-binding partner 5 to yield the detector-analyte complexes 6, 7 and 8.

The incubation time is dependent on the temperature and the concentration of the detector-binding partner 5. With PS2 as antibody, at a temperature of 37° C. and a concentration of detector-binding partner 5 of 0.1 to 1,000 μg/ml the incubation time is 1 to 120 minutes. An incubation time of 10 minutes for the detector-binding partner concentration of 5 μg/ml is optimal.

The solution containing the detector-analyte complexes 6, 7 and 8 is then brought in contact with the surface 9, which contains different immobilized capture-binding partners at the distinct surface regions 10, 11 and 12 (FIG. 2*a*).

The first surface region 10 exposes the immobilized capture-binding partner, which specifically recognizes ACT or the epitope 4 in the PSA-ACT complex 8 but not free PSA. Epitope 4 and ACT do not exist in complexes 6 and 7. The detector-PSA-ACT complex 8 can also form a sandwich 15 with PCT-ACT. Suitable for this part of the assay are, for example, the polyclonal antibodies against ACT from either rabbit or sheep (DPC Biermann). Alternatively, a monoclonal anti-ACT antibody can also be used, such as clone 8e6, 22h9/33 or ACT 14c7 (DPC Biermann).

The surface region 11 exposes an immobilized capture-binding partner, which specifically recognizes the hK2 specific epitope 3 (depicted as triangle in FIG. 1). The immobilized capture site binds the detector-binding partner 5-hK2 complex 7 to form sandwich 14 (FIG. 2*a*, center). Examples of suitable capture-binding partners are antibodies, which are raised according to Tindall et al. as described in U.S. Pat. No. 5,526,639 or WO 95/0334.

The immobilized capture-binding partner on surface region 12 recognizes the epitope 2, which exclusively exists as part of fPSA. This capture-binding partner binds to the detector-binding partner 5-fPSA complex 6 and thus forms sandwich 13 (FIG. 2*a*, lower left). An antibody suitable for the sandwich formation is antibody PS1 (HyTest). Other antibodies can also be used if they specifically recognize fPSA and bind with the detector-binding partner 5, such as the antibody 8a6 (HyTest).

The surface regions for the assay of the above-mentioned analytes can be designed with different characteristics. Such an alternative setup is outlined in FIG. 2*b*.

In this version, a capture-binding partner is immobilized on the surface region 10 (FIG. 2*b*, top right). It recognizes an epitope, which is present both in fPSA and in PSA-ACT. In addition, the capture-binding partner forms sandwich 13' with the detector-binding partner 5-fPSA complex 6 as well as sandwich 15' with the detector-binding partner 5-PSA-ACT complex 8. This is accomplished using the antibody 5g6 (HyTest). This surface region 10 captures total PSA (tPSA), i.e. the sum of free PSA and PSA-ACT complexes.

The version also features surface regions 11 and 12 with the above-described capture-binding partners. The velocity with which the detector-analyte complex binds to the capture-binding partners is crucial for the quantitative assay. tPSA is assayed on the first binding region 10, and fPSA is measured on the third binding region 12. The quantity of PSA complexes can be calculated as the difference between total and free PSA.

The time- and space-resolved binding of detector-analyte complexes to the capture-binding partners is determined. For this purpose, the apparatus as described in DE 19628002 and DE 19711281 may be used. Thus, a value can be obtained for the binding velocity; the dimension is mV/s. Dependent on the analyte concentration in the sample, typical values range from 10 to 10,000 mV/s.

As depicted in FIG. 3, a labeled binding partner is chosen as detector-binding partner 5, which recognizes a binding site 1 that is common to all three analytes. In addition to the detector-binding partner 5, a third binding partner 16 is added to the sample. Binding partner 16 is specific for fPSA. Therefore, two binding partners bind to the analyte fPSA during incubation. The binding between detector-fPSA complex 17 and the capture-binding partner yields the complex 18. In contrast to the steps depicted in FIGS. 2*a* and 2*b* for the binding to the immobilized binding partner, the formation of complex 18 occurs via the third binding partner 16, not the fPSA molecule.

EXAMPLE

The example describes the assay method according to this invention for fPSA, tPSA and PSA-ACT.

1. Binding Partners

The monoclonal antibody PS2 against PSA is used as detector-binding partner. This antibody recognizes the PSA epitope 3 and consequently binds to fPSA and the PSA-ACT complex. In the following, this antibody is referred to as detector-antibody. The monoclonal antibodies PS1 and 5g6 against PSA (both HyTest) are used as capture-binding partners. Clone PS1 exclusively recognizes fPSA; clone 5g6 recognizes an epitope, which is present in both, fPSA and PSA-ACT. In the following, these antibodies are referred to as capture-antibodies.

2. Labeling of the Detector-Antibodies 1 mg of the monoclonal antibody PS2 against PSA (HyTest) at a concentration of 1 mg/ml was incubated with 95 μg of the fluorescent dye S 0458 (FEW Wolfen) in 20 μl DMSO (Sigma) and stirred for 20 minutes at room temperature. The reaction mixture is then purified by FPLC (Åkta purifier, Amersham Pharmacia Biotech) using a column (Hi Trap Desalting, Amersham Pharmacia Biotech). In this procedure, about 0.01-15 dye molecules were coupled to each antibody (more precisely, 2-6 dye molecules).

3. Immobilization of the Capture-Antibodies

On a prism made of polymethylacrylate (PMMA, commercially available from Leica) a line of 11 confluent droplets is dispensed. Each droplet has a volume of 20 nl and consists of a solution of the anti-PSA antibody, clone PS1, with a concentration of 0.5 mg/ml PBS buffer (pH=7.4, 500 mM sodium chloride). This line of droplets forms the first surface region.

11 droplets with a volume of 20 nl are then arranged in a parallel line the same way as described above. However, in this line the antibody in the buffer solution is the anti-PSA antibody, clone 5g6. This creates the second surface region.

When the lines are dry, the prism is placed in an apparatus as described in DE 196 28 002. This places the immobilized capture-antibodies in the flow channel of the sensor.

4. Establishing a Calibration Curve

The calibration was done using known analyte concentrations. Commercially available fPSA (Quartett, 7820-0604) and PSA-ACT complex (DPC Biermann, BA 1022) were used in the assay. In the following, these analytes are referred to as antigens.

For the calibration, labeled anti-PSA antibodies and known amounts of allergens were used. 50 μl of the labeled anti-PSA antibody clone S2, at a concentration of 6 μg/ml were mixed with 50 μl aliquots of allergen solutions, which contained known concentrations of fPSA or PSA-ACT complex in PBS buffer, containing 1% BSA. The mixture was incubated for 10 minutes at 35° C. Table 1 lists the concentrations that have been used for the calibration.

The sets of calibration solutions with different allergen concentrations are then assayed using the biosensor. The binding of the detector-antigen complex to the specific surface regions causes an increase in fluorescence (LIF), which is measured using a photo multiplier voltage of 700 V. The measurement follows the procedure published by Meusel et al., Anal. Chem. 1999, 71, 5430-5435, DE 19628002 and DE 19711281. The apparatus as described in WO 01/77645A1 can be used for the measurement.

Figure 5:
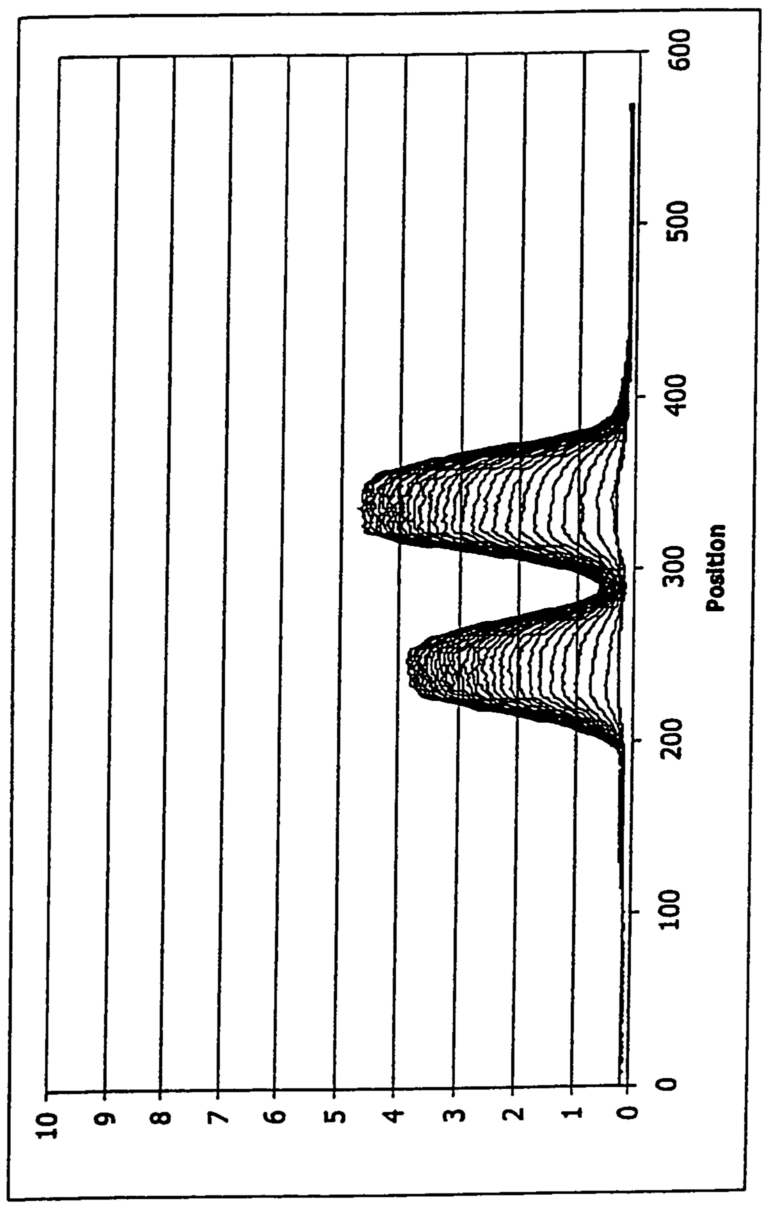
FIG. 5 is a diagram showing the calibration data (1) and (2) for the fPSA and tPSA (total PSA) assay.

In this assay arrangement, both, the first binding region with the immobilized anti-PSA antibody PS1 and the second binding region with the immobilized anti-PSA antibody 5g6 can bind fPSA. Therefore, the detector-fPSA complex binds to both, the first and second binding region during calibration for the fPSA antigen. FIG. 5 shows the time-resolved increase of the fluorescence signal due to the binding of the detector-fPSA complexes at the first surface region (positions 200-300) and the second surfach region (positions 300-400). The measured data in FIG. 5 are used to establish the calibration functions (1) and (2) (see below).

The detector-PSA-ACT complex binds to the second surface region with the immobilized anti-PSA antibody 5g6 only. For the calibration with PSA-ACT, only this second surface region recognizes detector-PSA-ACT complexes aside from also recognizing detector-fPSA complexes.

Figure 6:
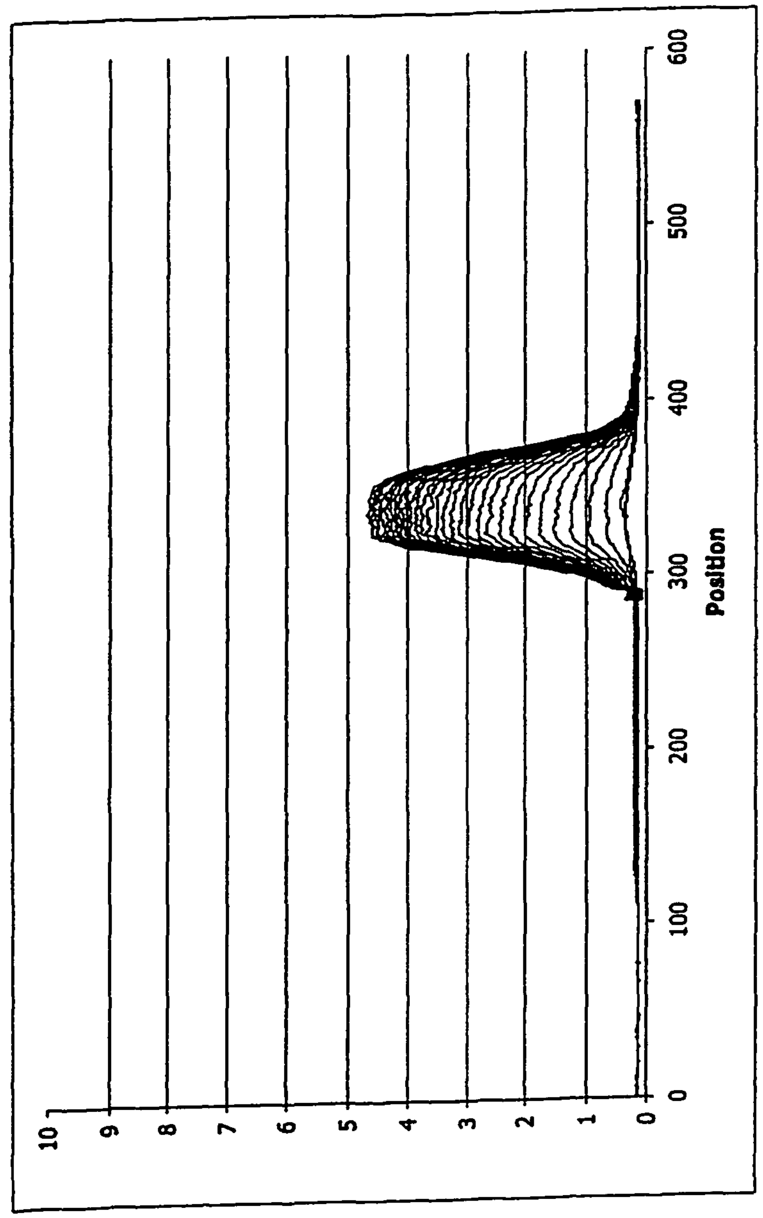
FIG. 6 is a diagram showing the calibration data (3) for the fPSA and tPSA assay.

FIG. 6 shows the time-resolved increase of the fluorescence signal due to the binding of the detector-PSA-ACT complexes to positions 300-400 at the second surface region. Surface region 1 is specific for the binding of detector-fPSA complexes. Therefore, there is no binding of detector-PSA-ACT complexes to surface region 1. FIG. 6 shows the data for the calibration function (3) (see below).

Figure 7:
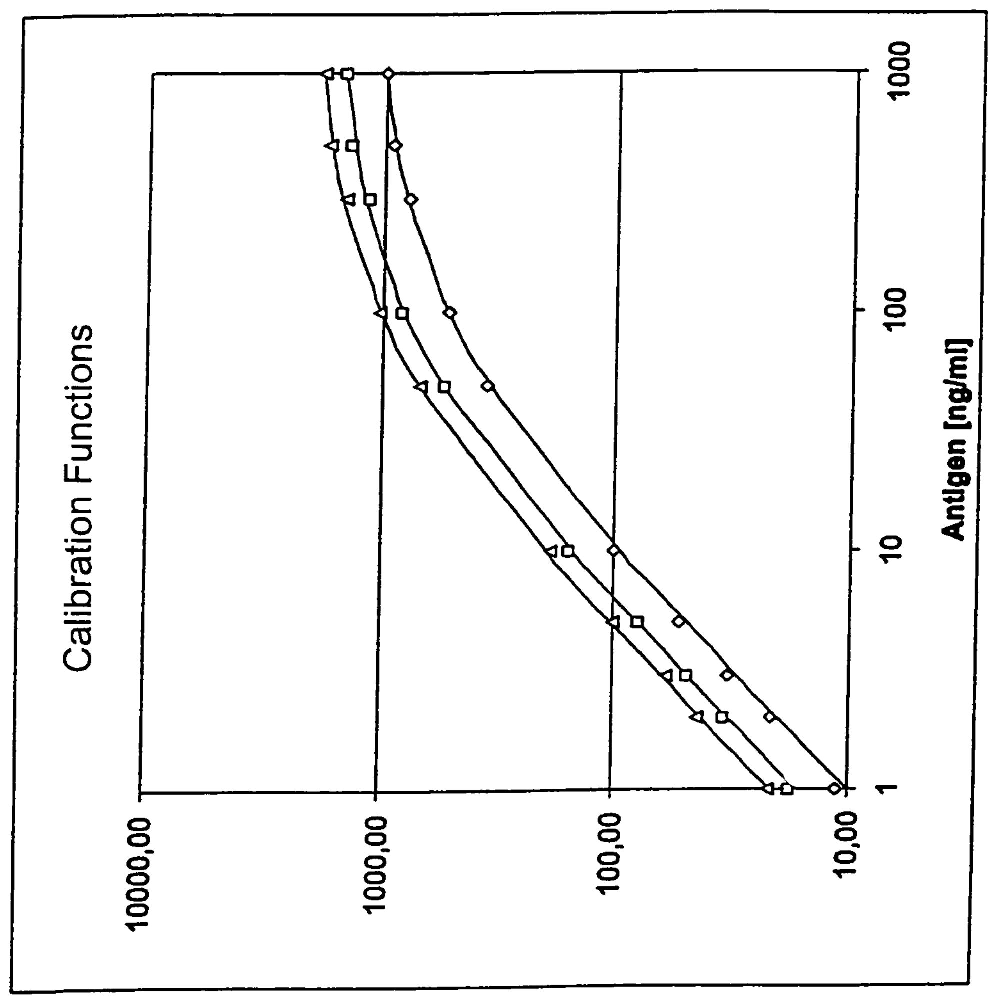
FIG. 7 is a diagram showing the velocities for the binding of detector-fPSA complexes and detector-PSA-ACT complexes to the capture-binding partner.

According to these data, the velocities for the concentration-dependent binding of the different detector-antigen complexes are determined separately for each of the two surface regions. The increase in the signal correlates with the concentration-dependent binding velocity. Important is therefore the signal increase over time, not the absolute signal amplitude. The data are delineated in Table 1 and in FIG. 7.

TABLE 1

| Concentration of fPSA or PSA-ACT* [ng/ml] | Binding of fPSA to PS1 [mV/s] | Binding of fPSA to 5g6 [mV/s] | Binding of PSA-ACT to PS1 [mV/s] | Binding of PSA-ACT to 5g6 [mV/s] |
|---|---|---|---|---|
| 1 | 11.39 | 17.45 | 0 | 21.71 |
| 2 | 21.10 | 33.53 | 0 | 43.18 |
| 3 | 31.87 | 48.55 | 0 | 58.80 |
| 5 | 51.88 | 78.14 | 0 | 98.63 |
| 10 | 99.38 | 156.1 | 0 | 185.9 |
| 50 | 360.5 | 548.9 | 0 | 696.5 |
| 100 | 526.5 | 838.3 | 0 | 1,058 |
| 300 | 788.1 | 1,191 | 0 | 1,481 |
| 500 | 923.1 | 1,406 | 0 | 1,717 |
| 1,000 | 1,004 | 1,494 | 0 | 1,859 |

In each case, the concentration refers to the immunochemically determined PSA.

The formula for the following three calibration functions was determined to be $$c_x = \frac{A_i * S_{x-y}}{B_i - S_{x-y}}$$

The symbols in this formula are defined as follows:

$c_x$=analyte concentration x in the solution, $S_{x-y}$=binding velocity of the analyte x to the surface region y B, A=parameters for the binding function, x=index for the analyte y=index for the surface region, i=index for the calibration curve.

$$c_{fPSA} = \frac{A_1 * S_{fPSA\text{-}PS1}}{B_1 - S_{fPSA\text{-}PS1}} \quad (1)$$

in this formula $A_1$=109.000 ng/ml and $B_1$=1,107.93 mV/s;

$$c_{fPSA} = \frac{A_2 * S_{fPSA\text{-}5g6}}{B_2 - S_{fPSA\text{-}5g6}} \quad (2)$$

in this formula $A_2$=99.6353 ng/ml and $B_2$=1,645.45 mV/s;

$$c_{fPSA\text{-}ACT} = \frac{A_3 * S_{PSA\text{-}ACT\text{-}5g6}}{B_3 - S_{PSA\text{-}ACT\text{-}5g6}} \quad (3)$$

in this formula $A_3$=95.7948 ng/ml and $B_3$=2,023.62 mV/s.

The following formulas were applied to calculate the concentrations, which use the parameters for the calibration functions.

$$S_{fPSA\text{-}PS1} = \frac{c_{fPSA} * B_1}{A_1 + c_{fPSA}} \quad (4)$$

$$S_{fPSA\text{-}5g6} = \frac{c_{fPSA} * B_2}{A_2 + c_{fPSA}} + \frac{c_{PSA\_ACT} * B_3}{A_3 + c_{PSA\text{-}ACT}} \quad (5)$$

$$S_{fPSA} = \frac{A_1 * S_{fPS1\text{-}PS1}}{B_1 + S_{fPS1\text{-}PS1}} \quad (6)$$

$$S_{fPSA\text{-}5g6} = \frac{c_{fPSA} * B_2}{A_2 + c_{fPSA}} \quad (7)$$

$$c_{fPSA\text{-}ACT} = \frac{S_{fPSA\text{-}5g6} - S_{PSA\text{-}ACT\text{-}5g6} * A_3}{S_{PSA\text{-}ACT\text{-}5g6} - B_3} \quad (8)$$

5. fPSA and tPSA Assay in an Unknown Sample

The assay in an unknown sample was done like the assay to obtain the calibration functions. However, instead of a standard solution with known amounts of antigen a test sample with an unknown concentration of these antigens was used.

50 μl of an unknown sample were incubated with 50 μl of a solution containing the labeled detector-anti-PSA antibody, clone PS2, at a concentration of 6 μg/ml for 10 minutes at 35° C. The solution is then put into the biosensor and the increase in fluorescence is measured at a photomultiplier voltage of 700 V. The fluorescence is caused by the binding of the detector-antigen complexes to their specific surface regions.

Figure 8:
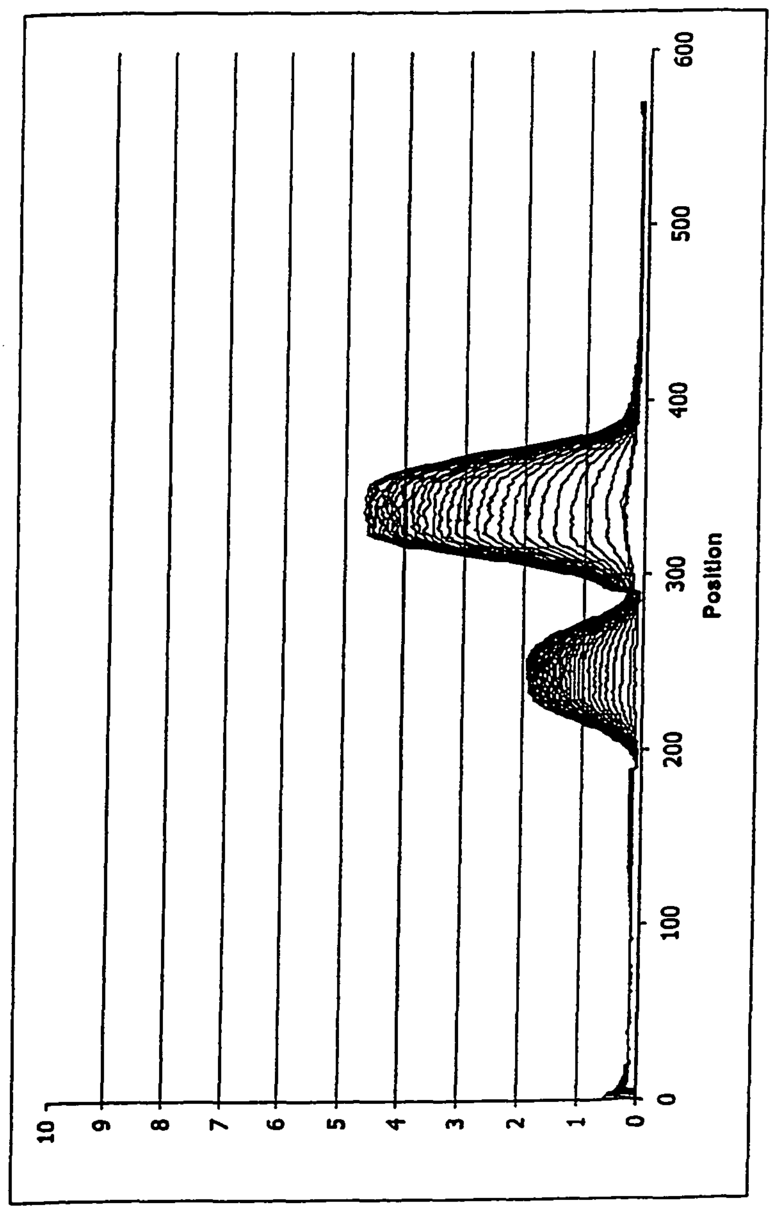
FIG. 8 is a diagram showing correlation of assay data for the determination of unknown amounts of fPSA and tPSA in a sample.
Figure 9:
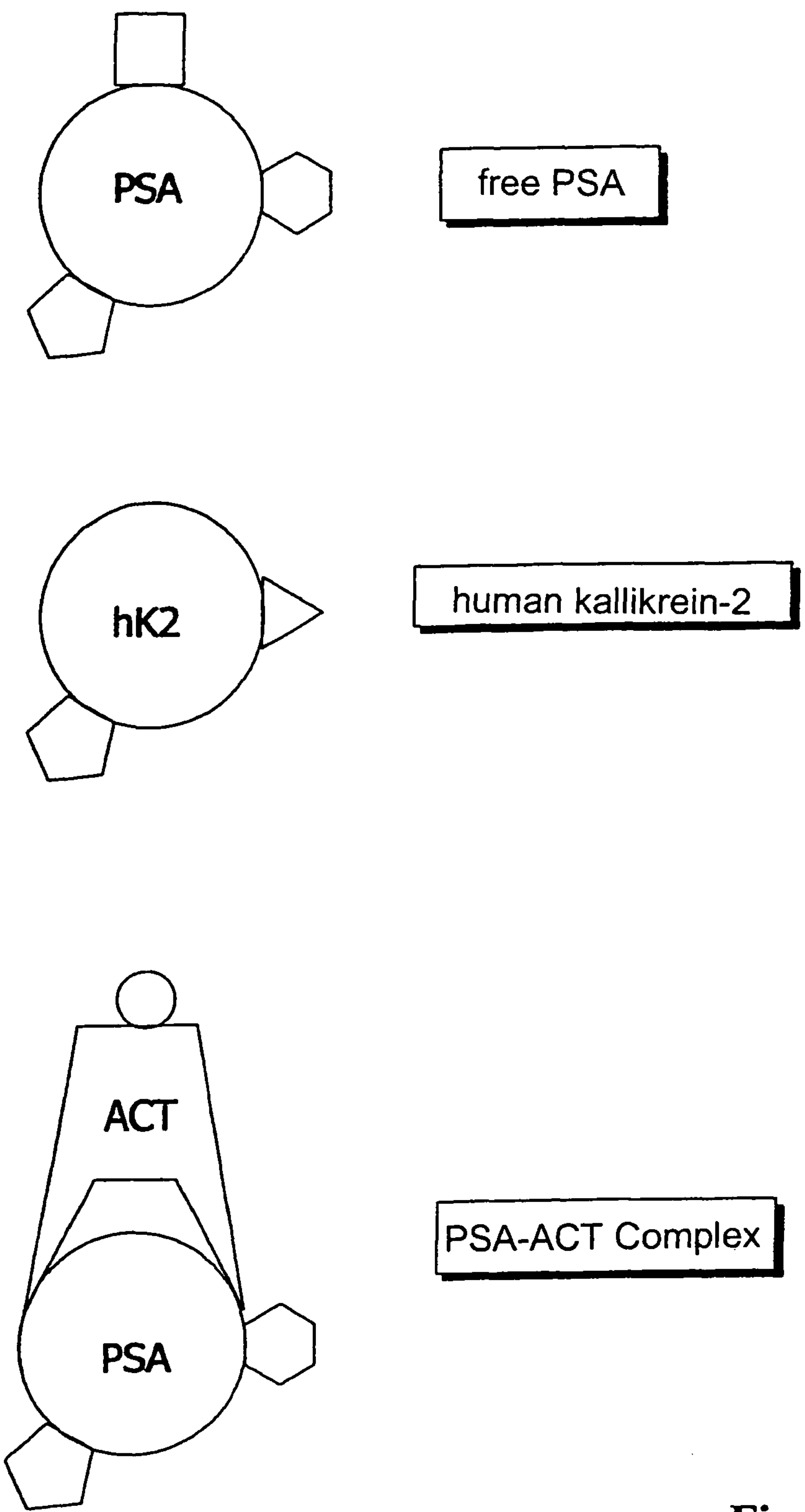
FIG. 9 is a symbol legend showing the meaning of the symbols usded in FIGS. 1 through 4.

The data are shown in FIG. 8. For the first surface region with immobilized PS1 (positions 200-300) the binding velocity is found to be 14.8 mV/s, and for the second surface region with immobilized 5g6 (positions 300-400) the binding velocity is 540 mV/s.

The interpretation of the data is based on the fact that fPSA and PSA-ACT bind independently of each other to the second surface region while the first surface region binds only fPSA. First, the concentration of fPSA on the first surface region is determined. The binding velocity (y) of 14.8 mV/s corresponds to a concentration of 1.5 ng/ml fPSA (see equation 6).

fPSA binds to both surface regions. This must be considered when calculating the PSA-ACT concentration, which binds only to the second surface region. The ascent for the binding curve for PSA-ACT on the second surface region must be corrected for the fPSA binding.

The 1.5 ng/ml fPSA, which have bound to the first binding region, contributes 24.0 mV/s to the binding on the second binding region (see formula 7). It follows that 24.0 mV/s of the signal on the second binding region is contributed by the binding of fPSA, while 516 mV/s (=540 mV/s−24.0 mV/s) are based on PSA-ACT binding.

According to the calibration for PSA-ACT at the second binding region this corresponds to the binding of PSA-ACT at a concentration of 34.8 ng/ml.

There is an alternative to the above-described calibration. The method above is based on the binding of fPSA to the first surface region and the binding of fPSA and PSA-ACT to the second surface region. This is followed by a calculation for the PSA-ACT binding to the second surface region.

A mixture of fPSA and PSA-ACT is used for the alternative calibration method. The binding of fPSA from this mixture to the first surface region as well as the binding of both, fPSA and fPSA-ACT to the second region are measured. However, a larger deviation of the PSA-ACT concentration from the standard mixture results in a lower precision for the PSA-ACT assay.

What is claimed is:

1. A method for the quantitative assay of fPSA, PSA-ACT and hK2, comprising the steps of:

(a) adding a labeled detector-binding partner to a test sample with the analytes fPSA, PSA-ACT and hK2 to form detector-analyte complexes that each consist of one analyte molecule and one detector molecule of said detector binding partner;

(b) binding the detector-analyte complexes from step (a) to three capture-binding partners to form detector-analyte-capture complexes, wherein each capture-binding partner is specific for one of the detector-analyte complexes; and, (c) measuring the time-resolved formation of detector-analyte-capture complexes.

2. A method for the quantitative assay of fPSA, PSA-ACT and hK2 comprising the steps of:

(a) adding a labeled detector-binding partner to a test sample with fPSA, PSA-ACT and hK2 to form detector-analyte complexes that each consist of one analyte molecule and one detector molecule of said detector binding partner;

(b) binding the detector-analyte complexes obtained in step (a) to three capture-binding partners to form detector-analyte-capture complexes, wherein the first of the capture-binding partners is specific for detector-fPSA complexes, the second of the capture-binding partners is specific for detector-hK2 complexes and the third of the capture-binding partners is bindable to detector-fPSA complexes and detector-PSA-ACT complexes; and, (c) measuring the time-resolved formation of detector-analyte-capture complexes.

3. A method for the quantitative assay of fPSA and PSA-ACT, comprising the steps of:

(a) adding a labeled detector-binding partner to a test sample with fPSA and PSA-ACT to form detector-analyte complexes that each consist of one analyte molecule and one detector molecule of said detector binding partner;

(b) binding the detector-analyte complexes formed in step (a) to two capture-binding partners to form detector-analyte-capture complexes, wherein one of the capture-binding partners is specific for detector-fPSA complexes and the other capture-binding partner binds detector-fPSA complexes as well as detector-PSA-ACT complexes; and, (c) measuring the time-resolved formation of detector-analyte-capture complexes.

* * * * *